(12) United States Patent
Sharif

(10) Patent No.: US 6,531,480 B1
(45) Date of Patent: Mar. 11, 2003

(54) NON-PEPTIDE BRADYKININ RECEPTOR ANTAGONISTS FOR USE IN TREATING OPHTHALMIC DISEASES AND DISORDERS

(75) Inventor: Najam A. Sharif, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/647,640

(22) PCT Filed: Mar. 4, 1999

(86) PCT No.: PCT/US99/04866

§ 371 (c)(1),
(2), (4) Date: Oct. 2, 2000

(87) PCT Pub. No.: WO99/51245

PCT Pub. Date: Oct. 14, 1999

Related U.S. Application Data
(60) Provisional application No. 60/080,003, filed on Apr. 3, 1998.

(51) Int. Cl.[7] .............................................. A67K 31/435
(52) U.S. Cl. ........................................ 514/277; 514/912
(58) Field of Search .................................. 514/277, 912

(56) References Cited

U.S. PATENT DOCUMENTS 5,270,050 A  12/1993  Coquelet et al. ............. 424/427

FOREIGN PATENT DOCUMENTS

| EP | 0 529 499 A1 | 8/1992 |
| JP | 10316677 | 12/1998 |

OTHER PUBLICATIONS

Campbell, William B., "Lipid–Derived Autoacoids: Eicosanoids and Platelet–Activating Factor," Goodman and Gilman's *The Pharmacological Basis of Therapeutics*, Pergman Press, NY, pp. 600–617, 1990.
Friedlander, Mitchell H., "Current Concepts in Ocular Allergy," *Annals of Allergy*, vol. 67:5–13, Jul., 1991.
Abelson, et al., "Conjunctivitis of Allergic Origin: Immunologic Mechanisms and Current Approaches to Therapy," *Survey of Ophthalmology*, vol. 38(Supplement):115–132, Jul.–Aug. 1993.
Proud, et al., Inflammatory Mediator Release on Conjunctival Provocation of Allergic Subjects with Allergen, *J. Allergy Clin Immunol*, vol. 85:896–905, May 1990.
Wiernas, et al, "Effects of Bradykinin on Signal Transduction, Cell Proliferation, and Cytokine, Prostaglandin $E_2$ and Collagenase–1 Release from Human Corneal Epithelial Cells," *Journal of Pharmacology*, vol. 123:1127–1137, 1998.
Diaz–Flores, et al., "Angiogenesis: an update," *Histology and Pathology*, vol. 9:807–843, 1994.
Regoli, et al., "Pharmacology of Bradykinin and Related Kinins," *Pharmacological Reviews*, vol. 32:1–46; 1980.

Hall, Judith M., "Bradykinin Receptors: Pharmacological Properties and Biological Roles," *Pharmac. Therapy*, vol. 56:131–190; 1992.
Sharma, J.N., "Therapeutic Prospects of Bradykinin Receptor Antagonists," *Gen. Pharmac.*, vol. 24(2):267–274, 1993.
Ma, et al., "Expression and Cellular Localization of the Kallikrein–Kinnin System in Human Ocular Tissues," *Exp. Eye Research*, vol. 63:19–26, 1996.
Belmonte, et al., "Neurobiology of Ocular Pain," *Progress in Retinal and Eye Research*, vol. 16(1):117–156, 1997.
Cole, et al., "Action of Bradykinin on Intraocular Pressure and Pupillary Diameter," *Ophthalmology Research*, vol. 6:308–314, 1974.
Elliot, et al., "RMP–7, a Bradykinin Agonist, Increases Permeability of Blood–Ocular Barriers in the Guinea Pig," *Investigative Ophthalmology & Visual Science*, vol. 36(12):12542–2547, Nov. 1995.
Regoli, et al., "New Selective Bradykinin Receptor Antagonists and Bradykinin $B_2$ Receptor Characterization," *Trends in Pharmacol. Science*, vol. 11:156–161, Apr. 1990.
Abe, et al., "A Novel Class of Orally Active Non–Peptide Bradykinin $B_2$ Receptor Antagonists. 1. Construction of the Basic Framework," *J. Med. Chem.*, vol. 41:564–578, 1998.
Salvino, et al., "Design of Potent Non–Peptide Competitive Antagonists of the Human Bradykinin $B_2$ Receptor," *Journal of Medicinal Chemistry*, vol. 36:2583–2584, 1993.
Cheronis, et al., "Design, Synthesis, and in vitro Activity of Bis(succinimido)hexane Peptide Heterodimers with Combined $B_1$ and $B_2$ Antagonist Activity[1,2]", *Journal of Medicinal Chemistry*, vol. 37(3):348–355, 1994.
Cheronis, et al., "A New Class of Bradykinin Antagonists: Synthesis and in vitro Activity of Bissuccinimidoalkane Peptide Dimers[1,2]", *Journal of Medicinal Chemistry*, vol. 35(9):1563–1572, 1992.
Srivastava, et al., "Hybrid Peptides Having Mixed Substance P (NK1), Neurokinin A (NK2) and Bradykinin (BK2) Antagonist Properties," *Immunopharmacology*, vol. 33:194–196, 1996.
Mavunkel, et al., "Synthesis and Characterization of Pseudopeptide Bradykinin B2 Receptor Antagonists Containing the 1,3,8–Triazaspiro[4.5]decan–4–one Ring System," *Journal of Medicinal Chemistry*, vol. 39(16):3169–3173, 1996.
Sharif, et al., "The Neuropeptide Bradykinin Stimulates Phosphoinositide Turnover in HSDM1C1 Cells: $B_2$–Antagonist–Sensitive Responses and Receptor Binding Studies," *Neurochemical Research*, vol. 18(12):1313–1320, 1993.

(List continued on next page.)

*Primary Examiner*—Zohreh Fay
(74) *Attorney, Agent, or Firm*—Sally S. Yeager

(57) ABSTRACT

This invention relates to the topical ocular use of non-peptide bradykinin receptor antagonists for the treatment of human ocular pain, neovascularization, corneal haze, allergy and inflammatory diseases.

8 Claims, No Drawings

OTHER PUBLICATIONS

Sharif, et al., "Identification of $B_2$–Bradykinin Receptors in Guinea Pig Brain Regions, Spinal Cord and Peripheral Tissues," *Neurochemical International*, vol. 18(1):89–96, 1991.

Sharif, et al., "Pharmacological Characterization of Bradykinin Receptors Coupled to Phosphoinositide Turnover in SV–40 Immortalized Human Trabecular Meshwork Cells," *Exp. Eye Research*, vol. 63:631–637, 1996.

Berridge, et al., "Lithium Amplifies Agonist–Dependent Phosphatidylinositol Responses in Brain and Salivary Glands," *Biochem J.*, vol. 206:587–595, 1982.

Matsuo, et al., "Clinical Applications of Anginin in Ophthalmology," *Acta Medicinae Okayama*, vol. 21(2):59–66, Apr. 1967.

Hu, et al., "[$Leu^8$]des–$Arg^9$–bradykinin Inhibits the Angiogenic Effect of Bradykinin and Interleukin–1 in Rats," *British Journal of Pharmacology*, vol. 109(1):14–17, May 1993.

Wirth, et al., "The Bradykinin $B_2$ Receptor Antagonist WIN 64338 Inhibits the Effect of des–$Arg^9$—bradykinin in Endothelial Cells," *European Journal of Pharmacology—Molecular Pharmacology Section*, Section 288, R1–R2, Jan. 1994.

NON-PEPTIDE BRADYKININ RECEPTOR ANTAGONISTS FOR USE IN TREATING OPHTHALMIC DISEASES AND DISORDERS

This Application is a 371 of PCT/US99/04866 filed on Mar. 4, 1999, which claims the benefit of Provisional application Ser. No. 60/080,003, filed Apr. 3, 1998.

The present invention relates to the topical ocular use of non-peptide bradykinin receptor antagonists for the treatment of human ocular pain, neovascularization, corneal haze, allergy and inflammatory diseases.

BACKGROUND OF THE INVENTION

Inflammation from cellular stress can cause excessive tissue damage. Numerous biochemical pathways are known to lead to inflammation. In general, these include the generation of locally produced or inflammatory cell derived proinflammatory cytokines (e.g., $IL_1$, $IL_6$, $IL_8$ and $TNF_\alpha$), as well as products from the cyclooxygenase system, such as prostaglandins, and the lipoxygenase system, such as leukotrienes, "HETEs" and "HPETEs." Other pro-inflammatory mediators released by mast cells (e.g., histamine, platelet activating factor) cause vascular permeability increases which in turn lead to the presence of yet more pro-inflammatory agents (e.g., bradykinin) at the site of trauma/allergic reaction. See generally, *Goodman and Gilman's The Pharmacological Basis of Therapeutics*, pages 600–617, Pergman Press, NY (1990). Therapies designed to inhibit the production of these types of agents and/or the blockade of the receptors mediating their effects are therefore of great interest.

Ocular allergic inflammation is a condition which generally causes patient discomfort including red eye, conjunctival edema and congestion, ocular discharge as well as scratchiness and itchiness. Ocular inflammation can be initiated by various insults. For example, ocular inflammation can result from allergic response to various allergens, bacterial infections, trauma to the eye, dry eye and surgical complications. Various anti-inflammatory therapies are currently in use for the treatment of ocular inflammation including the topical administration of diclofenac.

Allergic conjunctivitis affects over 25% of the general population (Friedlander, *Ann. Allergy*, volume 67, pages 5–13 (1991)). Human ocular allergic pathophysiology is mediated via several cellular and molecular mechanisms involving mast cells (Abelson and Schaefer, *Survey Ophthalmology*, volume 38, pages 115–132 (1993)). Once the conjunctival mast cells are activated by allergens, pollutants, airborne chemicals or pathogens, they rapidly liberate numerous inflammatory mediators (e.g., histamine and prostanoids) into the tear-film. These released agents, in turn, increase conjunctival vascular permeability and permit infiltration of additional pro-inflammatory agents such as bradykinin and inflammatory cells on the ocular surface (Abelson and Schaefer, *Survey Ophthalmology*). The net result of these events is generalized inflammation, edema, redness and itching—the cardinal signs of allergic conjunctivitis (Abelson and Schaefer, *Survey Ophthalmology*). Proud et al. (*J. Allergy Clin. Immunol.*, volume 85, pages 896–905 (1990)) have shown that 0.2 µM bradykinin is present in the tear-film of ocular allergic patients exposed to allergens, and that bradykinin can mimic the symptoms of allergic conjunctivitis.

Antihistamines (alone or in combination with alpha-adrenergic vasoconstrictors) and corticosteroids are currently used to treat some of the symptoms of allergic conjunctivitis and corneal/conjunctival inflammation. These drugs, however, have serious disadvantages and side-effects (e.g., low potency, short duration of action, discomfort and increases in intraocular pressure) which limit their clinical utility. Thus, new anti-allergy agents with improved efficacy and fewer side-effects are still needed.

Ocular surgery can result in various post-surgical inflammatory complications of the eye. Such complications generally include: 1) loss of vascular blood barrier function; 2) neutrophil accumulation; 3) tissue edema including conjunctiva swelling, conjunctiva congestion and corneal haze; 4) cataract formation; 5) cellular proliferation; and 6) loss of membrane integrity including decrease in docosahexaenoic acid levels in membrane phospholipids.

Another pathology which can affect the eye is neovascularization or angiogenesis. Angiogenesis is a term used to describe the development of new blood vessels or neovascularization (L. Diaz-Flores et al., *Angiogenesis: an Update, Histology and Histopathology*, volume 9, pages 807–843 (1994)). Though angiogenesis is a normal process for the development or maintenance of the vasculature, pathological conditions (i.e., angiogenesis dependent diseases) arise where blood vessel growth is actually harmful. Such pathologies include diabetic retinopathies, proliferative vitreoretinopathies, psoriasis, artritis and tumor development. The progression of angiogenesis occurs in several phases which include: elaboration of the angiogenic signal; dissolution of the blood vessel basement membrane; endothelial cell proliferation; endothelial cell migration; and formation and differentiation of capillary tubules and loops.

Recently, BK has been shown to be a potent cell proliferating stimulator in several cell types and tissues (Hall, *Pharmacol. Rev.*, Wiernas et al., *British J. Pharmacol.*, volume 123, pages 1127–1137 (1998)). As stated above, cellular proliferation is a critical component of the angiogenic response.

Angiogenesis is also associated with other important diseases of ocular tissue, especially in older patients and diabetics. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

Current therapy for the treatment of ocular neovascular disease is not very effective. Retinal neovascularization is often treated with multiple laser burns to the retina to remove the pathological vasculature. Patients with neovascular diseases of the anterior chamber (e.g. corneal neovascularization, iritis rubeosis) are treated with potent topical ocular glucocorticoids. These therapies are only partially effective and generally only slow neovascularization and the progress of the overall disease. In addition, they can cause severe side effects, including raising of intraocular pressure, if used over a relatively long period of time.

Other areas of ocular trauma relate to pain. Pain is a perceived nociceptive response to local stimuli in the body. The perception of pain at the level of the central nervous system requires the transmission of painful stimuli by peripheral sensory nerve fibers. Upon stimulation of tissue (i.e., thermal, mechanical or chemical), electrochemical signals are transmitted from the sensory nerve endings to the spinal column, and hence to the brain where pain is perceived.

The cornea is highly innervated with sensory afferents which transmit various painful stimuli to the central nervous system. Pain conditions involving the eye, therefore, can arise in numerous instances such as, foreign body stimulus, inflammation, dry eye syndrome, accidental trauma, surgical procedures and post-surgical recovery. For example, ocular pain can result from photorefractive keratotomy (PRK), a vision correcting, surgical procedure whereby a laser is used to shape the cornea. This process involves the photoablation of Bowman's membrane and the stromal levels of the cornea. As a result, the denuding of the nerve-containing epithelial layers of the cornea can cause some patients to experience pain following laser surgery until the epithelium regenerates.

Various therapies have been attempted for the alleviation of pain. The use of non-steroidal anti-inflammatory drugs (NSAIDs), such as diclofenac, have been developed to treat pain. These agents inhibit cyclooxygenase dependent prostaglandin synthesis. Prostaglandins can modulate pain perception at the level of the central nervous system and systemic administration of NSAIDs is known to provide analgesia. However, the use of NSAIDs can involve undesired side effects including gastrointestinal bleeding and kidney dysfunction.

Opiates are another class of compounds used to treat pain. Opiates can be administered in a number of ways. For example, opiates can be administered systemically, by intravenous injection or oral dosage, or locally, by subcutaneous, intramuscular or topical application. Opiates, however, have been associated with several problems including dose escalation (tolerance), addiction, respiratory depression and constipation.

Local anesthetics are another class of pain modulators which relieve pain by directly inhibiting nerve cellular function. One problem of local anesthetic therapy is the short duration of action. Furthermore, as local anesthetics cause non-specific membrane stabilization, they can have the undesired coincident effect of also inhibiting other biological functions, such as fibroblast and surrounding neuronal activity. Therefore, even though pain sensation can be abated with local anesthetic treatment, healing and normal function of the tissue may be significantly compromised.

Other agents have also been suggested for use in treating pain. Such agents include tricyclic antidepressants such as imipramine and desipramine, alpha-2 adrenergic agonists, serotonin uptake blockers, such as prozac, and other analgesics such as paracetamol, as described in U.S. Pat. No. 5,270,050 (Coquelet et al.). Some of these therapies, however, have been associated with side-effects such as dryness of mouth, drowsiness, constipation, and low potencies and efficacies.

A class of agents which potently and specifically inhibit the transmission of painful stimuli by sensory afferents without local anesthetic activity following topical ocular application has yet to be described.

Endogenous and exogenous bradykinin ("BK") induces inflammatory reactions, causes pain and may be implicated as a facilitator of corneal neovascularization and corneal haze, due its cell proliferating properties (Hall, *Pharmacol. Rev.;* Wiernas et al., *British J. Pharmacol.*).

Bradykinin is an endogenous peptide made up of nine amino acids (i.e., Arg-Pro-Pro-Gly-Phe-Ser-Pro-Phe-Arg). BK is found in many organs, including the eye. BK exhibits many biological effects in the body, including tissue contraction, fluid and ion secretion and pain inducement (Regoli and Barabe, *Pharmacol. Rev.,* volume 32, pages 1–46 (1980) and Hall, *Pharmacol. Ther.,* volume 56, pages 131–190 (1992)).

BK and another endogenous peptide, Lys-BK, bind to two major BK receptor-subtypes, namely $B_1$ and $B_2$, to produce their biological effects. The $B_2$-subtype is found to be expressed under normal physiological conditions, while the $B_1$-subtype is induced during injury or trauma (Regoli, and Barabe, *Pharmacol. Rev.,* and Hall, *Pharmacol. Ther.*). While the $B_1$-subtype has a low affinity for BK and a high affinity for Des-Arg$^9$-BK and Lys-BK, the $B_2$-subtype has a high affinity for BK and Lys-BK but a low affinity for Des-Arg$^9$-BK.

Both receptor subtypes have been cloned and shown to be coupled to G-proteins and phospholipase C, and their activation results in the generation of the second messengers inositol trisphosphate ("$IP_3$") and diacylglycerol ("DAG") (Hall, *Pharmacol. Ther.*). The signal transduction of BK receptor binding results in $IP_3$-stimulated mobilization of intracellular $Ca^{2+}$, followed by DAG phosphorylation of protein kinase C. Together, these events lead to final biological responses, such as fluid secretion (which can cause edema), pain, cell proliferation, etc.

The majority of the physiological and pathological effects of BK are mediated by the $B_2$-receptor-subtype. However, recent pharmacological evidence points to two additional BK-receptor subtypes, namely $B_3$ and $B_4$ (Hall, *Pharmacol. Ther.,* and Sharma, *Gen. Pharmacol.,* volume 24, pages 267–274, (1993)). The $B_3$ and $B_4$ receptor subtypes are actually stimulated by certain peptide BK antagonists, whereas the $B_1$ and $B_2$ subtypes are blocked by those antagonists (Sharma, *Gen. Pharmacol.*). While the presence of $B_3$ or $B_4$ receptor subtypes in the eye has not been investigated, it is believed they may be present since there is a robust BK-precursor and BK-generating enzyme pool in human ocular tissues and also the presence of the $B_1$ and $B_2$ receptors (Ma et al., *Exp. Eye Res.,* volume 63, pages 19–26, (1996)).

Administration of BK on the surface of animal eyes causes increased vascular permeability, hyperemia, edema and other signs of inflammation, and induction of pain messages (Belmonte et al., *Prog. Retinal and Eye Res.,* volume 16, pages 117–156 (1997)). Furthermore, high levels of BK and Lys-BK have been found in tears of ocular allergic patients challenged with an allergen (Proud et al., *J. Allergy Clin. Immunol.,* volume 85, pages 896–905 (1990)). Injection of BK in the eyes of animals (e.g. rabbits and guinea pigs) causes pupil constriction, increased permeability of blood-ocular barriers and increases intraocular pressure (Cole and Ungar, *Ophthalmol. Res.,* volume 6, pages 308–314 (1974); Elliot et al., *Invest. Ophthalmol. Vis. Sci.,* volume 36, pages 2542–2547 (1995)). Thus, there is evidence for the physiological and pathological effects of BK in the eye.

BK antagonists may have clinical utility for treating various diseases of the body including pain, rhinitis, asthma and arthritis (Hall, J. M., *Pharmacol. Ther.,* and Sharma, *Gen. Pharmacol.*). Most of the previously described BK antagonists, however, have been peptides of limited potency and selectivity (Regoli et al., *Trends in Pharmacol. Sci.,* volume 11, pages 156–161, 1990 and Hall, *Pharmacol. Ther.*). Peptides are labile, highly polar and, therefore, difficult to formulate and deliver to the site of treatment (Sharma, *Gen. Pharmacol.*). Such peptides would be especially difficult to formulate for topical administration to the eye due the relatively impenetrable thick scleral and corneal/conjunctival covering of the eye, especially when trying to treat inflammation/pain associated with tissues in the anterior and posterior chambers of the eye.

Nowhere in the art has it been disclosed, taught or suggested to use non-peptide BK antagonists to treat ocular pain, neovascularization, corneal haze and allergy and inflammation.

SUMMARY OF THE INVENTION

The present invention is directed to compositions and methods related to the treatment of ocular pain, neovascularization, corneal haze, allergy and inflammation. More specifically, the present invention is directed to topical ophthalmic compositions containing one or more non-peptide bradykinin receptor antagonists and methods of use in treating ocular pain, neovascularization, corneal haze, allergy and inflammation.

The compositions and methods of the present invention employ antagonists to bradykinin receptors which are relatively stable and bioavailable to the relevant ocular tissues. As stated above, previous BK antagonists have been peptides, which are labile and of low bioavailability. The present invention compositions, in contrast, are directed to stabile, bioavailable non-peptide BK antagonists.

DETAILED DESCRIPTION OF THE INVENTION

The present invention provides compositions, and methods of their use, for the treatment of ocular pain, neovascularization, corneal haze and ocular inflammation. More specifically, the present invention is directed to ophthalmic compositions comprising non-peptide bradykinin receptor antagonists and methods of use in treating ocular pain, neovascularization, corneal haze, allergy and inflammation.

While applicants do not wish to be bound by any theory, it is believed that BK causes inflammation and induces pain in the anterior and posterior chamber of the eye. It is also believed that BK is involved in angiogenic (i.e., causes retinal and corneal neovascularization) and corneal opacification processes due to its potent cellular proliferation properties. Thus, the administration of BK antagonists to the eye is thought to inhibit BK's receptor action, preventing the sequlea of pro-inflammatory effects and, hence, the consequential ocular diseases mentioned above.

Bradykinin receptors have been classified into at least four receptor subtypes. These subtypes include $B_1$, $B_2$, $B_3$ and $B_4$. Other subtypes may be elucidated in the future. For purposes of the present invention, all of these subtypes are included in the definition, "bradykinin receptor."

The compositions of the present invention will comprise one or more bradykinin receptor antagonists in a suitable pharmaceutical vehicle. As used herein, a "bradykinin antagonist" or "BK antagonist" refers to a compound of the present invention which inhibits the binding of bradykinin to a bradykinin receptor and therefore prevents activation of the receptor. The BK antagonists of the present invention are selected from various chemical classes, except linear monomeric peptide classes, e.g., HOE 140. Such classes of BK antagonists of the present invention include non-peptide BK antagonists, cyclic peptides antagonists, peptide dimer antagonists, cyclic organic molecule antagonists, peptido-mimetic antagonists, or other classes of BK antagonists which are not readily hydrolizable, in contrast to linear peptides. As used herein, the term "non-peptide BK antagonist" refers to those BK antagonists which are not linear, monomeric peptides.

Examples of organic non-peptide BK antagonists of the present invention include FR173657 ((E)-3-(6-acetamido-3-pyridyl)-N-[N-[2,4-dichloro-3-[(2-methyl-8-quinolinyl)oxymethyl]phenyl]-N-methylaminocarbonylmethyl] acrylamide); FR167344 (N-[N-[3-[3-bromo-2-methylimdazo[1,2-a]pyridin-8-yl)oxymethyl]2,4-dichlorophenyl]N-methylaminocarbonylmethyl]-4-(dimethylaminocarbonyl)cinnamylamide hydrochlroide); WIN-64338 ([4-{(2[{bis(cyclohexylamino) methylene}amino]-3-[2-naphthyl]-1-oxopropyl) amino}phenyl]methyl)tributylphosphonium chloride monohydrochloride); WIN-62318; CP-2458; and others described in Abe et al., *J. Med. Chem.*, volume 41, pages 564–578 (1998) and Salvino et al., *J. Med. Chem.*, volume 36, pages 2583–2584 (1993); the entire content of the foregoing publications are incorporated herein by reference to the extent such publications disclose non-peptide BK antagonists of the present invention.

Examples of bissuccinimide-alkane peptide dimer BK antagonists of the present invention include CP-0127, CP-0364, and other compounds described in Cheronis et al, *J. Med Chem.*, volume 37, pages 348–355 (1994); *J. Med. Chem.*, volume 35, pages 1563–1572 (1992); and Srivastava et al., *Immunopharmacol.*, volume 33, pages 194–197 (1996); the entire contents of the foregoing publications are incorporated herein by reference to the extent such publications disclose non-peptide BK antagonists of the present invention.

Other examples of psuedopeptide BK antagonists of the present invention include NPC-18521, NPC-18688 and others described in Mavunkel et al., *J. Med Chem.*, volume 39, pages 3169–3172 (1996), the entire contents of which is incorporated herein by reference to the extent such publication discloses non-peptide BK antagonists of the present invention.

The non-peptide BK antagonists of the present invention may also be readily elucidated by employing the following bradykinin receptor and/or cellular functional assays:

Bradykinin receptor binding assays. Sharif and Whiting have described this type of receptor binding assay in: Sharif and Whiting, *Neurochemical Res.*, volume 12, pages 1313–1320 (1993); and Sharif and Whiting, *Neurochem. Internat.*, volume 18, pages 89–96 (1991), the entire contents of which are incorporated herein by reference, and which may be modified as described below, for the elucidation of non-peptide BK antagonists of the present invention. Briefly, cells (e.g., HSDM1C1, TM3 or CEPI-17-CL4) or tissues (e.g., guinea pig ileum, lung or brain) bearing the constitutive $B_2$-BK receptor or cells genetically engineered to express such receptors, are harvested and gently homogenized in 25 mM TES (N-Tris[hydroxymethyl]methyl-a-aminoethansulfonic acid) buffer (pH 6.8, containing 1 mM 1,10 phenanthroline and a mixture of various peptide inhibitors (140 µg/ml bacitracin, 1 µM captopril, 1 mM dithiothreitol and 0.1% bovine serum albumin) using a Polytron tissue disruptor (setting "3–5" for 5–8 seconds). The homogenates are centrifuged at 30,000×g (20 minutes at 4° C.) and the cell pellets gently dispersed in the above-described TES buffer (at 10–30 mg wet weight tissue/ml) for the binding assay. The resuspended cell or tissue pellet homogenates (400 µl aliquots) are incubated with 50 µl of various concentrations of the test unlabeled, non-peptide BK antagonist candidate (1 pM–10 µM final concentrations) or buffer and 50 µl of [$^3$H]-BK (0.5 nM final concentration) in polypropylene tubes at 23° C. for 90 minutes in order to reach equilibriun. Non-specific binding is determined using 10 µM unlabeled BK. The assay is terminated by rapid vacuum filtration on a Tomtec cell harvester through Wallac "B" glass fiber filters (pre-soaked in 0.3% polyethyleneimine) using three 3 ml ice-cold 50 mM Tris HCl buffer (pH 7.4) washes. Receptor-bound radioactivity captured on the filter is measured by liquid scintillation spectrometry on a Wallac Beta-scintillation counter. Data analysis is performed using a standard non-linear, iterative curve-fitting computer program to determine the affinity ($K_i$, defined as the concentration required to inhibit [$^3$H]-BK binding by 50% and indicating the ability of the compound to bind to the receptor) of the BK antagonist for the BK receptor. BK antagonists having a $K_i \leq 1 \times 10^{-7}$M (i.e., affinity $\geq$ 100 nM) are within the non-peptide BK antagonist definition of the present invention.

Cellular functional assay. Sharif and Xu have described this type of functional assay in: Sharif and Xu, *Exp. Eye Res.*, volume 63, pages 631–637 (1996), the entire contents of which are incorporated herein by reference, and which may be modified as described below, for the elucidation of the BK antagonists of the present invention. Briefly, cells bearing the constitutive $B_2$-BK receptor (e.g., HSDM1C1, TM3 or CEPI-17-CL4) or cells genetically engineered to express such receptors are grown in sterile 24-well culture plates and are incubated with [$^3$H]-myo-inositol (2 µCi/ml; 15–17 Ci/mmol) in sterile culture medium for 24 hours at 37° C. in order to label the cell membrane phosphoinositide lipids. The medium is then aspirated and the cells exposed to BK in sterile culture medium (15 mM HEPES buffer) containing 10 mM LiCl for 60 minutes at 37° C. in order to facilitate the accumulation of [$^3$H]-inositol phosphates ([$^3$H]-IPs) (Berridge et al., *Biochem. J.*, volume 206, pages 587–595 (1982)). To determine the potency and/or efficacy of a non-peptide BK antagonist candidate, the candidates are added (1 pM–10 µM final concentrations) to the cells 30 minutes prior to the addition of BK (e.g., 1 µM final concentration). The medium is aspirated at the end of the incubation, and the assay terminated by the addition of 1 ml of ice-cold 0.1M formic acid and the [$^3$H]-IPs quantified by standard ion exchange chromatography (Berridge et al., 1982) and liquid scintillation spectrometry on a beta-counter. Data analysis is performed using a standard non-linear, iterative curve-fitting computer program to determine the potency ($K_i$, defined as the concentration required to inhibit the BK-induced [$^3$H]-IPs accumulation by 50% and indicating the ability of the antagonist to block the agonist-induced functional response) of the BK antagonist for the BK receptor. BK antagonists with a $K_i \leq 1 \times 10^{-7}$ M (i.e., potency $\geq$ 100 nM) are within the non-peptide BK antagonist definition of the present invention.

Preferred BK antagonists of the present invention are those antagonists which are: 1) potent BK antagonists; 2) relatively hydrophobic for topical uptake and rapid penetration; 3) non-labile; and 4) exhibit a low occurrence of side-effects. In general, BK antagonists which inhibit the activation of the $B_2$ receptor are the most preferred BK antagonists of the present invention. Examples of $B_2$ receptor antagonists include FR173657 ((E)-3-(6-acetamido-3-pyridyl)-N-[N-[2,4-dichloro-3-[(2-methyl-8-quinolinl)xymethyl]phenyl]-N methylaminocarbonylmethyl] acrylamide); FR167344 (N-[N-[3-[3-bromo-2-methylimdazo[1,2-a]pyridin-8-yl)oxymethyl]2,4-dichlorophenyl]N-methylaminocarbonylmethyl]-4-(dimethylaminocarbonyl)cinnamylamide hydrochlroide); WIN-64338 ([4-{(2[{bis(cyclohexylamino) methylene}amino]-3-[2-naphthyl]-1-oxopropyl) amino}phenyl]methyl)tributylphosphonium chloride monohydrochloride); WIN-62318, CP-2458, CP-0127, CP-0364, NPC-18521 and NPC-18688.

As used herein, the term "pharmaceutically effective amount" refers to that amount of one or more non-peptide BK antagonist(s) of the present invention, which reduces, stabilizes or ameliorates ocular pain, neovascularization, corneal haze, allergy or inflammation. The compounds of the present invention can be administered as solutions, suspensions, or emulsions (dispersions or gels), including ointments, in a suitable ophthalmic vehicle. The preferred route of administration is topical.

In preparing present invention compositions for topical administration, the BK antagonists are generally formulated from about 0.00005 to about 0.5 percent by weight (wt %). The BK antagonists are preferably formulated between about 0.0003 to about 0.3 wt % and, most preferably, between about 0.0005 and about 0.03 wt %. In general, the compositions will be solutions, having a pH between 4.5 to 7.4. While the precise regimen is left to the discretion of the clinician, the resulting solution or solutions are preferably administered by placing one drop of each solution(s) in each eye one to four times a day as needed, or as directed by the clinician.

Other ingredients which may be desirable to use in the ophthalmic preparations of the present invention include preservatives, co-solvents, buffers, viscosity building agents and penetration enhancers. Viscosity building agents, such as hydroxymethyl cellulose, hydroxyethyl cellulose, methylcellulose, polyvinylpyrolidine, or the like, may be added to the compositions of the present invention to improve the retention of the compound in the conjunctival sac or surrounding area. In order to prepare sterile ophthalmic ointment formulations, the BK antagonist may be combined with a preservative in an appropriate vehicle, such as white petroleum, mineral oil or liquid lanolin. Sterile ophthalmic gel formulations may be prepared by suspending the BK antagonist in a hydrophilic base prepared from the combination of, for example, carbopol-940, or the like, according to the methods known in the art for other ophthalmic formulations. Other compositions of the present invention may contain penetration enhancing agents such as cremephor and tween 80, in the event the BK antagonists are less penetrating in the eye.

As used herein, the term "pharmaceutically acceptable ophthalmic vehicle" refers to those vehicles which cause at most, little to no ocular irritation, provide suitable preservation if needed, and deliver one or more non-peptide BK antagonists of the present invention in a homogenous dosage.

Preferred formulations of BK antagonists of the present invention include the following Examples 1–4:

EXAMPLE 1

| Ingredient | Amount (wt %) |
| --- | --- |
| BK antagonist | 0.001 |
| Phosphate Buffered Saline | 1.0 |
| Benzalkonium Chloride | 0.01 |

-continued

| Ingredient | Amount (wt %) |
|---|---|
| Polysorbate 80 | 0.5 |
| Purified water | q.s. to 100% |

EXAMPLE 2

| Ingredient | Amount (wt %) |
|---|---|
| BK antagonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 3

| Ingredient | Amount (wt %) |
|---|---|
| BK antagonist | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 4

| Ingredient | Amount (wt %) |
|---|---|
| BK antagonist | 0.0005 |
| Phosphate Buffered Saline | 1.0 |
| Hydroxypropyl-β-cyclodextrin | 4.0 |
| Purified water | q.s. to 100% |

I claim:

1. A method for treating ophthalmic allergy diseases or disorders which comprises administering topically to the eye a composition comprising a therapeutically effective amount of a non-peptide bradykinin antagonist in a pharmaceutically acceptable ophthalmic vehicle.

2. The method of claim 1, wherein the non-peptide bradykinin antagonist is selected from the group consisting of FR173657 ((E)-3-(6-acetamido-3-pyridyl)N-[N-[2,4-dichloro-3-[(2-methyl-8-quinolinyl)oxymethyl]phenyl]-N-methylaminocarbonylmethyl]acrylamide); FR167344 (N-[N-[3-[3-bromo-2-methylimdazo[1,2-a]pyridin-8-yl)oxymethyl]2,4-dichlorophenyl]N-methyl-aminocarbonylmethyl]-4-(dimethylaminocarbonyl)cinnamylamide hydrochlroide); WIN-64338 ([4-{(2[{bis(cyclohexylamino)methylene}amino]-3-[2-naphthyl]-1-oxopropyl)amino}phenyl]methyl)tributylphosphonium chloride monohydrochloride); WIN-62318 and/or combinations thereof.

3. The method of claim 2 wherein the non-peptide BK antagonist is FR173657 ((E)-3-(6-acetamido-3-pyridyl)-N-[N-[2,4-dichloro-3-[(2-methyl-8-quinolinyl)oxymethyl]phenyl]-N-methylaminocarbonylmethyl]acrylamide).

4. The method of claim 1, wherein the non-peptide BK antagonist is elucidated using a bradykinin receptor antagonist assay or a cellular functional assay.

5. The method of claim 1, wherein the non-peptide BK antagonist is a $B_1$-BK antagonist.

6. The method of claim 1, wherein the non-peptide BK antagonist is a $B_2$-BK antagonist.

7. The method of claim 1, wherein the non-peptide BK antagonist is a $B_3$-BK antagonist.

8. The method of claim 1, wherein the non-peptide BK antagonist is a $B_4$-BK antagonist.

* * * * *